(12) United States Patent
Burbank et al.

(10) Patent No.: US 7,223,279 B2
(45) Date of Patent: *May 29, 2007

(54) METHODS FOR MINIMALLY-INVASIVE, NON-PERMANENT OCCLUSION OF A UTERINE ARTERY

(75) Inventors: Fred Burbank, Laguna Niguel, CA (US); Greig E. Altieri, Laguna Beach, CA (US); Michael L. Jones, Capistrano Beach, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 09/908,815

(22) Filed: Jul. 20, 2001

(65) Prior Publication Data

US 2002/0124853 A1  Sep. 12, 2002
US 2006/0000479 A9  Jan. 5, 2006

Related U.S. Application Data

(63) Continuation-in-part of application No. 09/556,934, filed on Apr. 21, 2000, now Pat. No. 6,550,482.

(60) Provisional application No. 60/279,477, filed on Mar. 28, 2001.

(51) Int. Cl.
*A61B 17/28* (2006.01)
(52) U.S. Cl. .................... 606/205; 600/424
(58) Field of Classification Search ........ 606/205–210, 606/157, 48, 158, 151, 142, 148, 119, 122; 600/500, 504, 453, 424
See application file for complete search history.

(56) References Cited

U.S. PATENT DOCUMENTS

| 2,400,251 A | 5/1946 | Nagel |
| 3,209,753 A | 10/1965 | Hawkins et al. |
| 3,411,505 A | 11/1968 | Nobis |
| 3,779,248 A | 12/1973 | Karman |
| 4,120,302 A | 10/1978 | Ziegler |

(Continued)

FOREIGN PATENT DOCUMENTS

DE    195 28 440 A    2/1997

(Continued)

OTHER PUBLICATIONS

Ravina et al., *Arterial Embolization to Treat Uterine Myomata*, Lancet, Sep. 9, 1995; vol. 346, pp. 671-672.

(Continued)

*Primary Examiner*—(Jackie) Tan-Uyen T. Ho

(57) ABSTRACT

Non-permanent occlusion of the uterine arteries is sufficient to cause the demise of uterine myomata without unnecessarily exposing other tissues and anatomical structures to hypoxia attendant to prior permanent occlusion techniques. A therapeutically effective transient time of occlusion of a uterine artery to treat uterine fibroid tumors is from 1 hours to 24 hours, and preferably is at least about 4 hours. A therapeutically effective temporary time of occlusion of a uterine artery to treat uterine fibroid tumors is from 1 day (24 hours) to 7 days (168 hours), and preferably is about 4 days (96 hours). By invaginating the tissues of the vaginal wall up to or around a uterine artery, collapse of the uterine artery can be achieved without penetrating tissue of the patient.

15 Claims, 6 Drawing Sheets

U.S. PATENT DOCUMENTS

| | | | |
|---|---|---|---|
| 4,192,313 A * | 3/1980 | Ogami | 606/207 |
| 4,226,240 A | 10/1980 | Walker, Jr. | |
| 4,292,960 A | 10/1981 | Paglione | |
| 4,428,379 A | 1/1984 | Robbins et al. | |
| 4,509,528 A | 4/1985 | Sahota | |
| 4,650,466 A | 3/1987 | Luther | |
| 4,757,823 A | 7/1988 | Hofmeister et al. | |
| 4,945,896 A | 8/1990 | Gade | |
| 4,994,069 A | 2/1991 | Ritchart et al. | |
| 5,037,430 A * | 8/1991 | Hasson | 606/119 |
| 5,081,997 A | 1/1992 | Bosley, Jr. et al. | |
| 5,108,408 A | 4/1992 | Lally | |
| 5,195,964 A * | 3/1993 | Kletzky et al. | 604/523 |
| 5,195,979 A * | 3/1993 | Schinkel et al. | 604/164.09 |
| 5,201,314 A | 4/1993 | Bosley et al. | |
| 5,226,911 A | 7/1993 | Chee et al. | |
| 5,275,166 A | 1/1994 | Vaitenkunas et al. | |
| 5,289,831 A | 3/1994 | Bosley | |
| 5,336,231 A | 8/1994 | Adair | |
| 5,383,922 A | 1/1995 | Zipes et al. | |
| 5,427,108 A | 6/1995 | Bollinger | |
| 5,456,693 A | 10/1995 | Conston et al. | |
| 5,458,596 A | 10/1995 | Lax et al. | |
| 5,488,958 A | 2/1996 | Topel et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,562,680 A * | 10/1996 | Hasson | 606/119 |
| 5,588,960 A | 12/1996 | Edwards et al. | |
| 5,614,204 A | 3/1997 | Cochrum | |
| 5,662,676 A | 9/1997 | Koninckx | |
| 5,662,680 A | 9/1997 | Desai | |
| 5,672,153 A | 9/1997 | Lax et al. | |
| 5,674,243 A | 10/1997 | Hale | |
| 5,691,314 A | 11/1997 | Hodgen | |
| 5,697,942 A | 12/1997 | Palti | |
| 5,713,371 A | 2/1998 | Sherman et al. | |
| 5,713,896 A | 2/1998 | Nardelia | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,759,154 A | 6/1998 | Hoyns | |
| 5,766,135 A | 6/1998 | Terwilliger | |
| 5,776,129 A | 7/1998 | Mersch | |
| 5,792,059 A | 8/1998 | Furia et al. | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,899,861 A | 5/1999 | Friemel et al. | |
| 5,910,484 A | 6/1999 | Haupert, Jr. | |
| 5,911,691 A | 6/1999 | Mochizuki et al. | |
| 5,916,173 A | 6/1999 | Kirsner | |
| 5,921,933 A | 7/1999 | Sarkis et al. | |
| 5,922,008 A * | 7/1999 | Gimpelson | 606/207 |
| 5,941,889 A | 8/1999 | Cermak | |
| 5,979,453 A | 11/1999 | Savage et al. | |
| 6,015,541 A | 1/2000 | Greff et al. | |
| 6,019,724 A | 2/2000 | Gronningsaeter et al. | |
| 6,032,673 A | 3/2000 | Savage et al. | |
| 6,033,398 A | 3/2000 | Farley et al. | |
| 6,034,477 A | 3/2000 | Peeters et al. | |
| 6,035,238 A | 3/2000 | Ingle et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,080,118 A | 6/2000 | Blythe | |
| 6,106,473 A | 8/2000 | Violante et al. | |
| 6,152,874 A | 11/2000 | Looney et al. | |
| 6,169,914 B1 | 1/2001 | Hovland et al. | |
| 6,175,751 B1 | 1/2001 | Maizes | |
| 6,210,330 B1 | 4/2001 | Tepper | |
| 6,231,515 B1 | 5/2001 | Moore et al. | |
| 6,254,601 B1 | 7/2001 | Burbank et al. | |
| 6,261,234 B1 | 7/2001 | Lin | |
| 6,280,441 B1 | 8/2001 | Ryan | |
| 6,293,954 B1 | 9/2001 | Fogarty | |
| 6,299,621 B1 | 10/2001 | Fogarty et al. | |
| 6,371,973 B1 * | 4/2002 | Tepper | 606/205 |
| 6,602,251 B2 | 8/2003 | Burbank et al. | |
| 6,905,506 B2 | 6/2005 | Burbank et al. | |
| 2002/0111537 A1 | 8/2002 | Taylor et al. | |
| 2002/0165579 A1 | 11/2002 | Burbank et al. | |
| 2002/0183771 A1 * | 12/2002 | Burbank et al. | 606/158 |
| 2002/0188306 A1 | 12/2002 | Burbank et al. | |
| 2003/0018270 A1 | 1/2003 | Makin et al. | |
| 2003/0120286 A1 * | 6/2003 | Burbank et al. | 606/142 |
| 2003/0120306 A1 | 6/2003 | Burbank et al. | |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 311 468 A | 1/1997 |
| WO | WO 95/02370 | 1/1995 |
| WO | WO 95/02371 | 1/1995 |
| WO | WO 98/19713 | 5/1998 |
| WO | WO 99/00057 | 1/1999 |
| WO | WO 01/68720 | 9/2001 |
| WO | WO 01/80713 | 11/2001 |
| WO | WO 02/00192 | 1/2002 |
| WO | WO 02/078521 | 10/2002 |

OTHER PUBLICATIONS

Hay, D.L., et al., *Hemostasis in Blood Vessels After Ligation*, Am. J. Obstet. Gynecol., Mar. 1989, 160:3, pp. 737-739.

Brohim, R.M., et al., *Development of Independent Vessel Security After Ligation With Absorbable Sutures or Clips*, Am. J. Surg., Mar. 1993, vol. 165, pp. 345-349.

Schaefer, C.J., et al., *Absorbable Ligating Clips*, Surg. Gynecol. Obstet., 1982, 154:513-6.

Barth, K., et al., "*Long Term Follow-up of Transcatheter Embolization with Autologous Clot, Oxycel and Gelfoam in Domestic Swince*", Investigative Radiology, May-Jun. 1977, vol. 12, No. 2, pp. 273-280.

Bateman, W., "*Treatment of Intractable Menorrhagia by Bilateral Uterine Vessel Interruption*", American Journal of Obstetrics & Gynecology, Jul. 15, 1994, vol. 89, No. 6, pp. 825-827.

Brigato, G., et al., *Tecnica strumentale non invasiva nelle emorragie irrefrenabili del post-partum* ("A Noninvasive Instrumental Method in Severe Postpartum Hemorrhages"), Minerva Ginecologica, 1998, vol. 50, No. 7-8, pp. 337-339. (translation attached).

Burbank, Fred, et al., *Uterine Artery Occlusion by Embolization or Surgery for the Treatment of Fibroids: A Unifying Hypothesis-Transient Uterine Ischemi*, The Journal of the American Association of Gynecologic Laparoscopists, Nov. 2000, vol. 7, No. 4 Supplement, pp. S3-S49. (previously provided during personal interview on Nov. 28, 2001 in co-pending U.S. Appl. No. 09/556,934).

Co-pending U.S. Appl. No. 09/556,934, filed Apr. 21, 2000; Inventor: Fred Burbank et al.

Fuchs, Karl, "Afibrinogenemia Treated by Ligation of Uterine Arteries", *Gynecologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

International Search Report for PCT/US02/23347 mailed Nov. 20, 2002.

International Search Report for PCT/US03/35815 mailed Jun. 30, 2004.

International Search Report for PCT/US2004/038111, mailed May 3, 2005.

Written Opinion for PCT/US2004/038111, mailed May 3, 2005.

International Preliminary Report of Patentability for Serial No. PCT/US04/01935, mailed Jul. 8, 2005.

International Search Report for PCT/US2004/38276 mailed Mar. 15, 2005.

\* cited by examiner

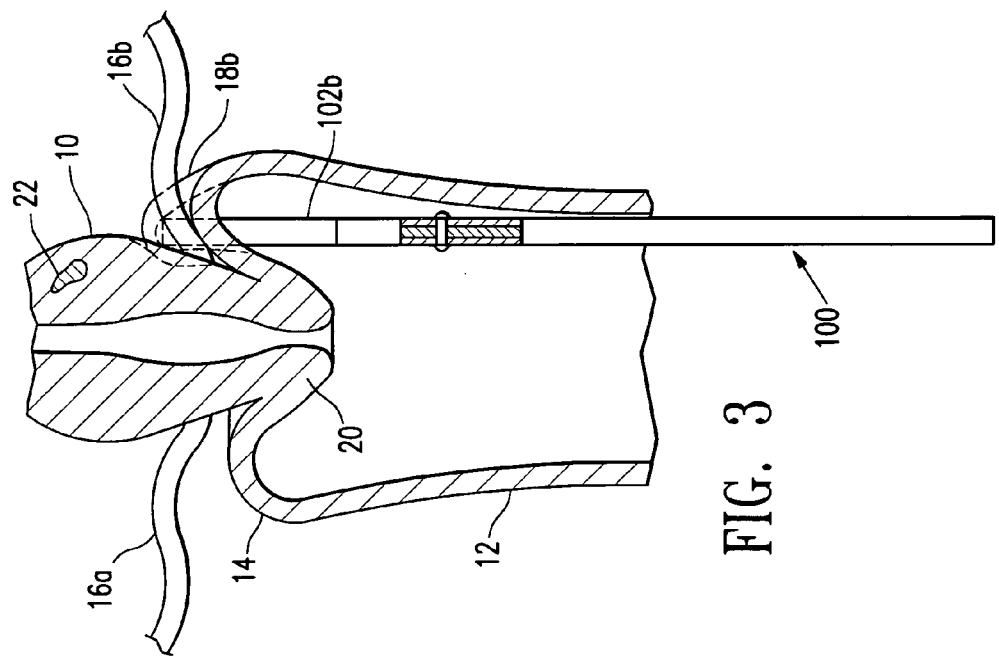
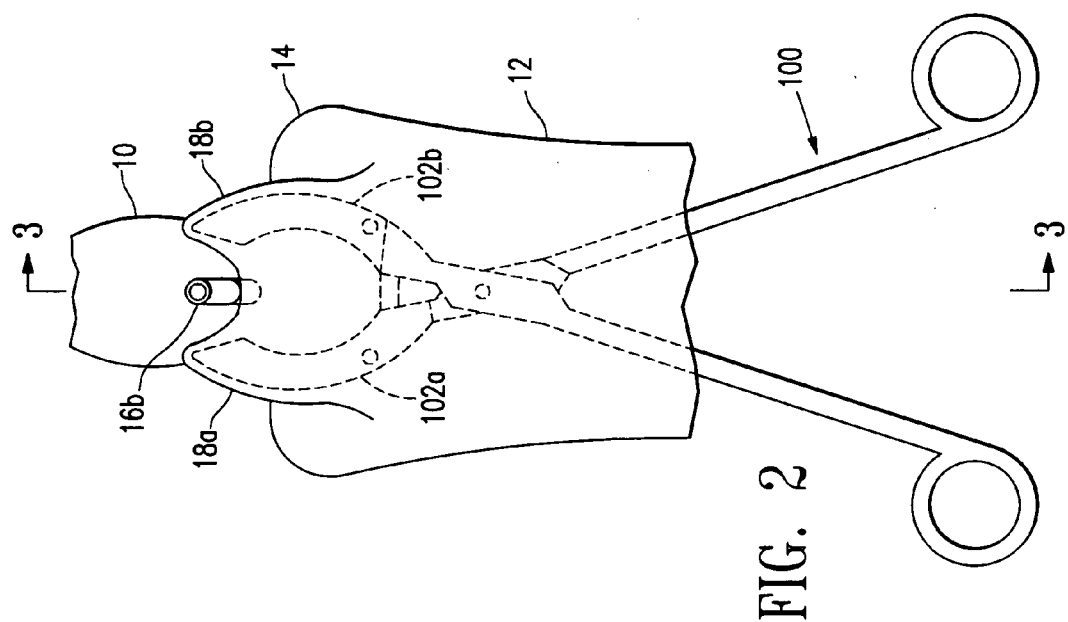

METHODS FOR MINIMALLY-INVASIVE, NON-PERMANENT OCCLUSION OF A UTERINE ARTERY

This application is a continuation-in-part of application Ser. No. 09/556,934, filed Apr. 20, 2000, now U.S. Pat. No. 6,550,482 (incorporated herein in its entirety by reference) and is based on provisional application Ser. No. 60/279,477, Mar. 28, 2001. Priority is claimed to both of the aforesaid applications.

BACKGROUND OF THE INVENTION

1. Field of the Invention

The present invention relates generally to the treatment of disorders which receive blood flow from the uterine arteries, and more particularly to methods for the non-permanent occlusion of the uterine artery or arteries, including for use in treating uterine myomata (fibroids), dysfunctional uterine bleeding (DUB), post partum hemorrhaging (PPH), and uterine bleeding associated with cesarian section surgery.

2. Brief Description of the Related Art

Hysterectomy (surgical removal of the uterus) is performed on approximately 600,000 women annually in the United States. For approximately 340,000 women, hysterectomy is probably the best current therapeutic choice for the treatment of their diseases (uterine cancer, endometriosis, menorrhagia, and prolapse). For approximately 60,000 women with dysfunctional uterine bleeding (abnormal menstrual bleeding that has no discrete anatomic explanation such as a tumor or growth), newer endometrial ablation techniques may be an alternative to hysterectomy. For approximately 200,000 women with benign but symptomatic (excessive bleeding, pain, and "bulk" sensations) muscular tumors of the uterus, known as leiomyoma or fibroids, newer treatment methods have been developed which may spare these women a hysterectomy, as well.

Hysterectomy for treating uterine fibroid disorders, though effective, has many undesirable characteristics. Thus, any method which can approximate the therapeutic result of a hysterectomy without removing the uterus (and commonly the ovaries since they are closely adjacent to the uterus) would be a significant improvement in this field.

The undesirable characteristics of hysterectomy include a known mortality rate of 0.5 deaths per 1000 hysterectomies. Stated another way, the risk of death within 30 days of hysterectomy is thirty times greater for women who have had a hysterectomy than for women of similar ages and backgrounds who have not had a hysterectomy. Morbidity (medical symptoms and problems short of death) associated with hysterectomy include possible injury to adjacent organs (the bladder, the ureters, and bowel), hospital stay of approximately one week, five to six weeks of slow recovery to normal activity, three weeks of absence from work, direct medical expenses of at least $10,000, indirect cost of time away from work, a future three-fold increase in the incidence of cardiovascular disease, decreased sexual pleasure in approximately thirty percent of women, and depression and anxiety for many years after the hysterectomy for approximately eight percent of women.

Surgically removing fibroids (myomectomy) or in situ ablation of uterine fibroids is a bit like eradicating ants in the pantry—they are not all seen from one perspective and there may be a lot of them. Commonly, a diagnosis of uterine fibroids involves the presence of multiple fibroids, often averaging ten fibroids or more per afflicted uterus. Consequently, it is difficult to know which fibroid is causing symptoms to the patient (bleeding, pain, and bulk effects on adjacent organs). Furthermore, fibroids occur at different layers in the uterus. Uterine fibroids can occur adjacent to the lining of the uterus (submucosal fibroid), in the myometrium (intramural fibroid), or adjacent to the outer layer of the uterus (subserosal fibroid). Consequently, if one is directly observing the uterus from the peritoneal cavity, only subserosal fibroids would be seen. If one is directly observing the uterus from the endometrial surface of the uterus, only the submucosal would be seen. Fibroids deep within the wall of the uterus are poorly visualized from either surface. Finally, since fibroids come in all sizes, only the larger fibroids will be seen in any case.

Clearly, the strategy of identifying which individual fibroid is causing symptoms (when there are often many), finding that fibroid, and then either removing or destroying that individual fibroid is a rather complex strategy. It is therefore easy to understand why the hysterectomy is such a common surgical choice. With hysterectomy, all uterine fibroids are removed in one stroke.

In 1995, it was demonstrated that fibroids, in a uterus that contained one or multiple fibroids, could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671–672, incorporated by reference in its entirety herein). This technique is known as "uterine artery embolization". The technique uses standard interventional radiology angiographic techniques and equipment, whereby the uterine arteries are accessed via a transvascular route from a common femoral artery into the left and right uterine arteries.

Three facts explain the success of uterine artery embolization. First, it has been established that pelvic bleeding from a wide variety of sources (e.g., auto accidents, surgical errors, and post partum hemorrhage) can be effectively controlled with embolization techniques using coils placed in arterial and venous lumens (U.S. Pat. Nos. 4,994,069, 5,226,911, and 5,549,824, all of which are incorporated in their entireties herein) (available from Target Therapeutics), or particles (GELFOAM pledgets, available from Upjohn, Kalamazoo, Mich., or IVALON particles, available from Boston Scientific).

Second, fibroids live a tenuous vascular life with very little ability to recruit a new blood supply from the host when the primary blood supply is compromised. Third, the uterus has a dual (or redundant) blood supply; the primary blood supply is from the bilateral uterine arteries, the secondary blood supply from the bilateral ovarian arteries.

Consequently, when both uterine arteries are occluded, i.e., bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms.

The uterine artery embolization technique utilized by Ravina et al. uses standard transvascular equipment, available in a typical interventional radiology angiography suite. This equipment includes guide catheters to selectively enter the tortuous right and left uterine arteries, Ivalon or Gelfoam particles, and intravascular coils. With skill and these standard angiographic tools, the uterine arteries can be occluded bilaterally and fibroid disease treated through a 2 mm hole in the right groin and through the right common femoral artery. Following the procedure, the arterial puncture site is held with manual pressure for fifteen minutes. While postprocedural pain is often significant, and requires intravenously delivered pain medication, the patient is typically fully recovered in a number of days.

The problem with uterine artery embolization is simple. The physicians who know how to do the procedure are interventional radiologists, who do not take care of gynecology problems. The physicians who take care of gynecology problems do not possess the skill necessary to perform catheter-based uterine artery embolization. Accordingly, only on the order of tens of thousands of uterine artery embolizations have been performed, worldwide, since approximately 1995, whereas hundreds of thousands of hysterectomies have been performed each year for uterine fibroids which are symptomatic.

Currently, many physicians continue to embolize the uterine artery with PVA particles. As reported by the Society for Cardiovascular and Interventional Radiology in late 1999, some 6000 cases have been performed within the United States. Currently the annualized run rate for this procedure is approximately 4500 cases per year.

Previously, physicians have permanently, surgically ligated the uterine artery utilizing metal vascular clips. This procedure has been performed laparoscopically and requires a great deal of surgical skill to access, identify, dissect, and ligate the uterine arteries. This requirement for high skill and a full surgical approach has limited the use of surgical ligation of the uterine arteries as a clinical alternative for uterine fibroid treatment.

The current treatments offered to women focus on permanent or near permanent occlusion methods for the uterine artery. These methods include (the expected longevity of the embolic agent is given parenthetically): embolizing with PVA particles (6 months to permanent in situ); embolizing with stainless steel coils (permanent in situ); embolizing with Gelfoam (3 to 4 weeks before degradation of the embolic particles); surgical ligation with metal vascular clips (permanent); and surgical ligation with RF ablation (permanent).

All of the prior art devices and methods are therefore aimed at permanent occlusion of the uterine artery, resulting in redirection of the blood flow to the uterus through collateral circulation. The patients which suffer most dramatically from uterine myomata are women of child bearing age who may desire to bear additional children. The current methods of embolizing or ligating uterine arteries are specifically contraindicated for women who desire to bear additional children. This is the realization of inadequate blood supply to the uterus because of the loss of the uterine arteries, the primary blood supply. A few reports have been cited of women who have undergone uterine artery embolization with PVA particles and then gone on to become pregnant and deliver normal babies. Reports have also been cited of women who have experienced premature menopause due to ovarian failure from these same procedures.

While it is apparent that uterine artery embolization with the current embolic agents or ligation techniques is effective for treating uterine myomata, it is also apparent from a review of case reports and complications that this treatment is in need of a substantial improvement in safety.

The tissue of the vaginal wall is very elastic, pliable, and flexible. The vaginal wall can made to assume different shapes without tearing and without significant patient discomfort or pain. Heretofore, this inherent characteristic of these tissues has not been utilized in the treatment of myomata, or for accessing the uterine artery. Instead, prior techniques have relied upon transvascular routes (Ravina et al.), complete surgical or laparoscopic dissection of the tissues surrounding a uterine artery to achieve access to the vessel. The difficulty and cost associated with the use of traditional transvascular access, and the possibility of infection and surgical complication associated with dissection, render these prior techniques unacceptable.

Those of skill in the art are well acquainted with DUB, PPH, and cesarian section-related bleeding. While the causes of DUB are often not identified, current treatments include endometrial ablation and hysterectomy, which can be extreme treatments for some patients. PPH and cesarian section-related bleeding can be a dangerous if not quickly and adequately controlled, which may require a fast surgical response, from which the patient may suffer from associated trauma of the surgery.

Another aspect of hysterectomy procedures is that the blood supply to the uterus is typically stopped by ligating the uterine arteries, to prevent the patient from bleeding excessively as the uterus is removed. This ligation task can be very laborious and time-consuming, as the arteries are dissected and ligated by the surgeon, and have associated complications.

There therefore still remains a need in the art for improvements in methods, processes, and techniques for occluding the uterine arteries for treatment of numerous conditions and/or facilitating other procedures.

SUMMARY OF THE INVENTION

According to a first exemplary embodiment, a process of treating a condition of a patient comprises the steps of non-invasively, non-permanently occluding a uterine artery for a therapeutically effective time period, and reestablishing blood flow through the uterine artery at the termination of said therapeutically effective time period.

According to a second exemplary embodiment, a process useful for treating a patient having at least one uterine artery and a uterus, the process comprises the steps of non-invasively, non-permanently occluding at least one uterine artery for a therapeutically effective time period and removing at least a portion of a uterus of a patient.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 2 illustrates a right side elevational view of portions of a uterus, vagina, uterine arteries, and an exemplary tool according to an exemplary embodiment of the invention;

FIG. 3 illustrates a cross-sectional view taken at line 3—3 in FIG. 2;

DESCRIPTION OF THE PREFERRED EMBODIMENTS

Figure 1:
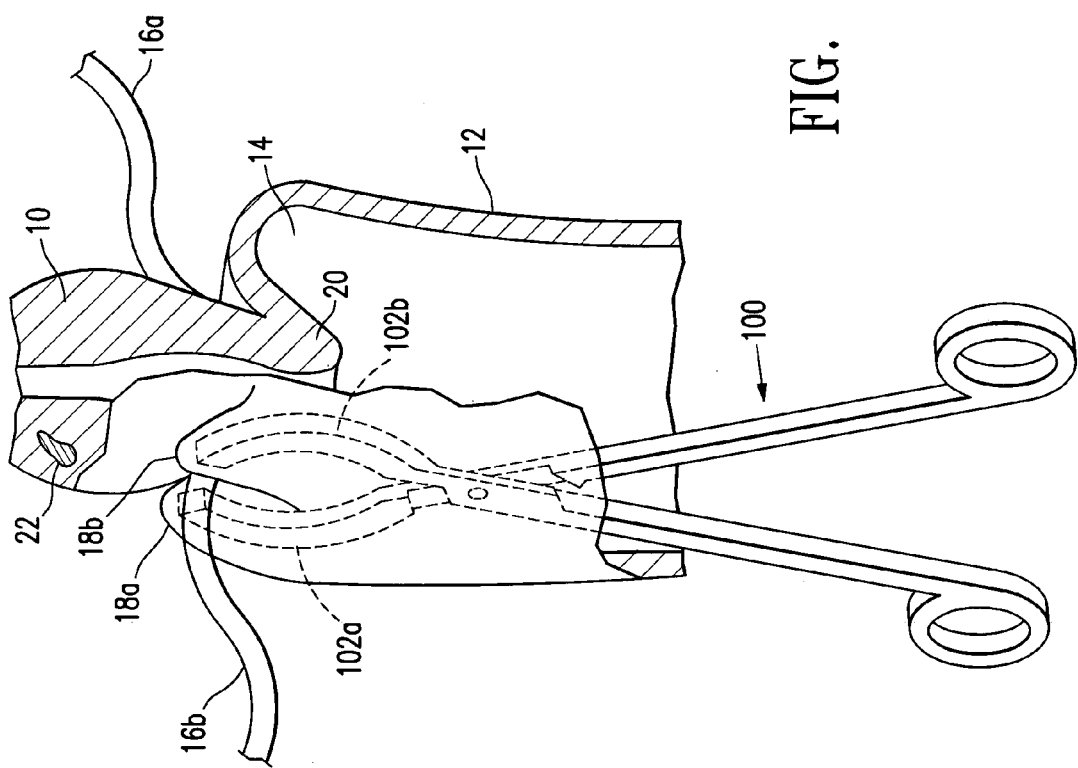
FIG. 1 illustrates a perspective view of portions of a uterus, vagina, uterine arteries, and an exemplary tool.
Figure 5:
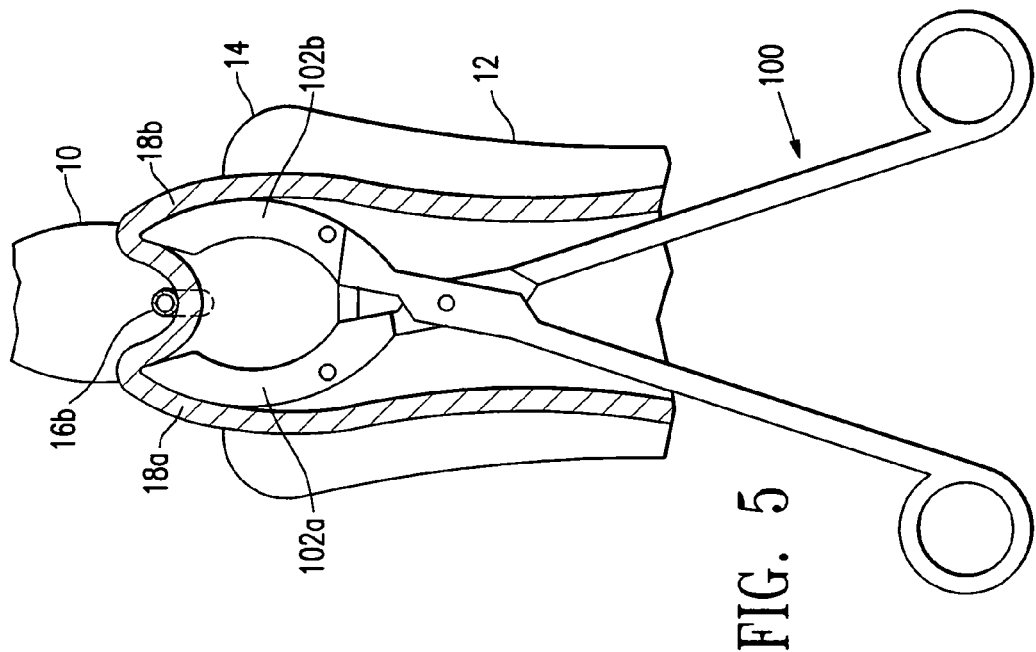
FIG. 5 illustrates a cross-sectional view taken at line 5—5 in FIG. 4.
Figure 4:
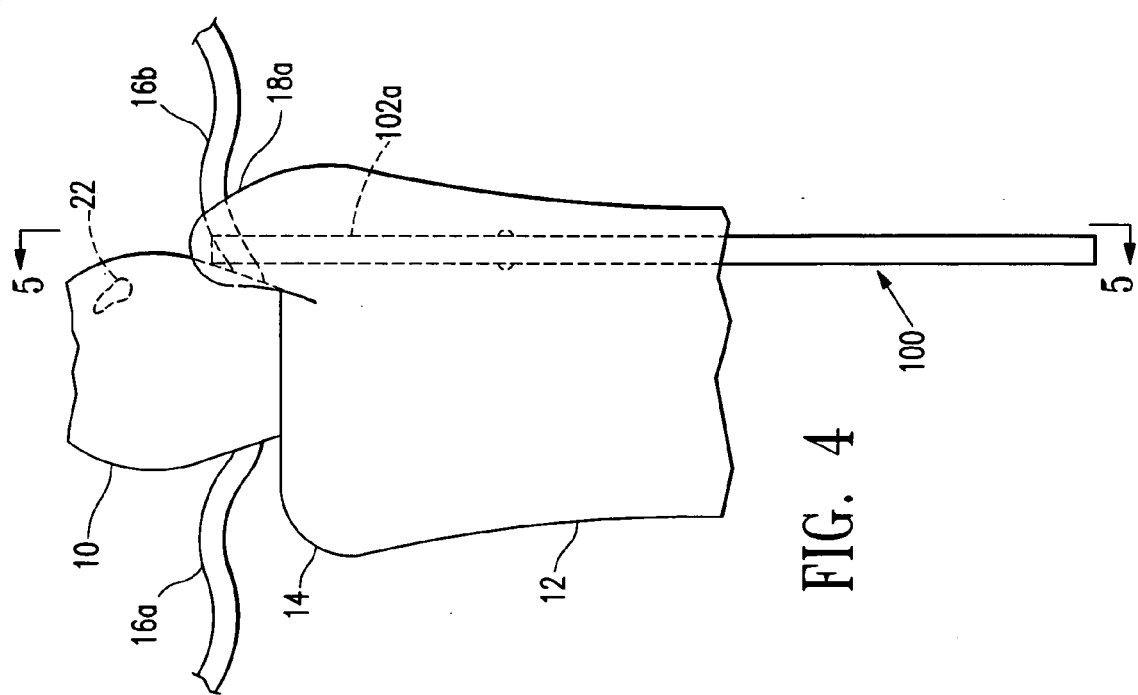
FIG. 4 illustrates a front elevational view of portions of a uterus, vagina, uterine arteries, and an exemplary tool.
Figure 7:
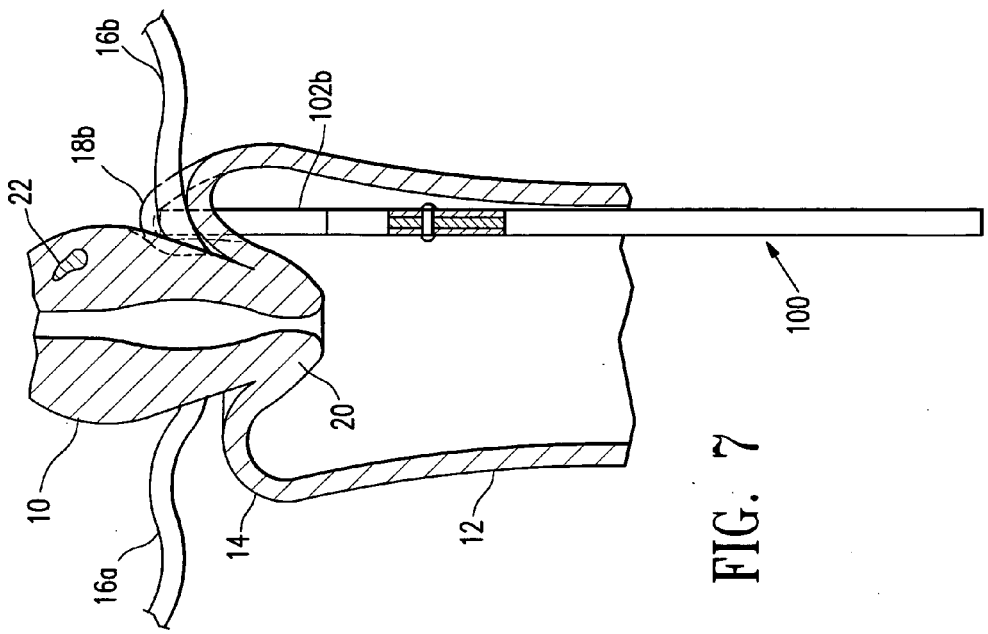
FIG. 7 illustrates a cross-sectional view taken at line 7—7 in FIG. 6.
Figure 6:
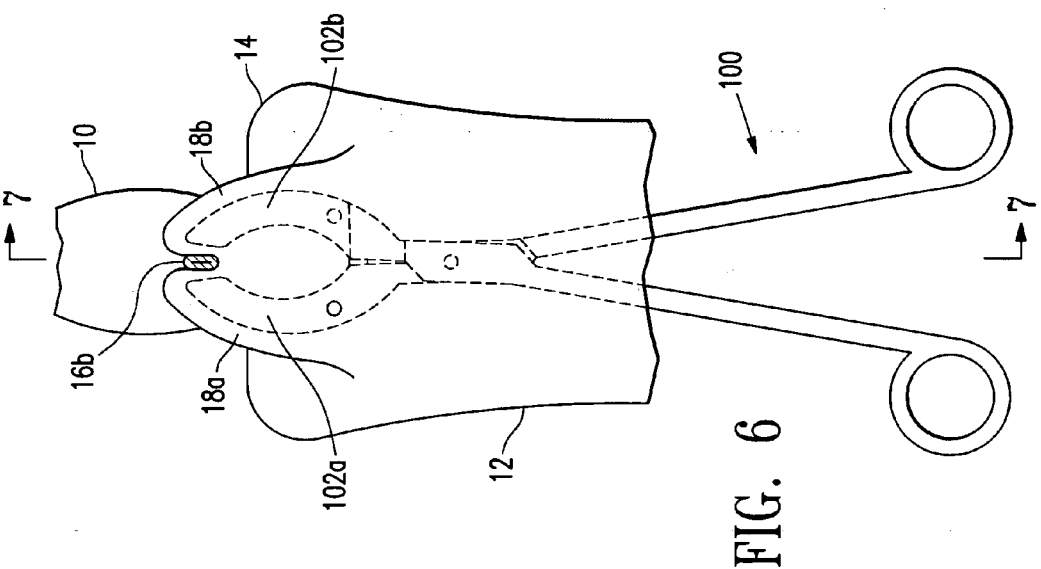
FIG. 6 illustrates a right side elevational view of portions of a uterus, vagina, uterine arteries, and an exemplary tool, during a clamping step.
Figure 9:
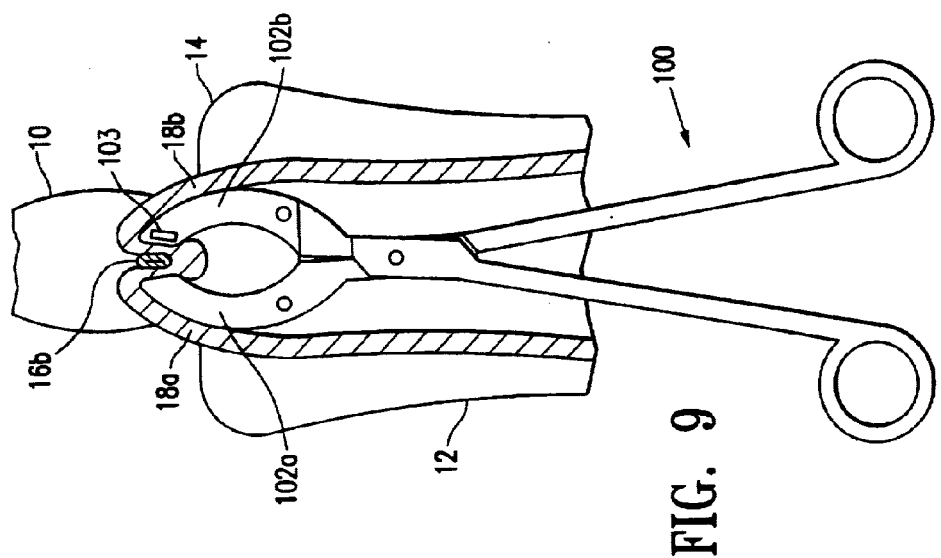
FIG. 9 illustrates a cross-sectional view taken at line 9—9 in FIG. 8.
Figure 8:
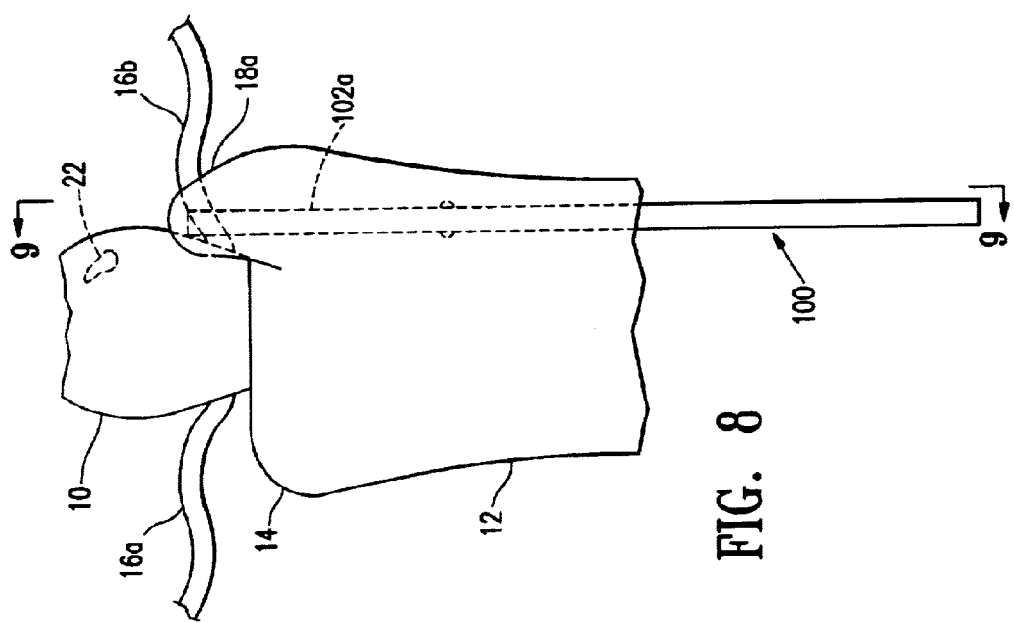
FIG. 8 illustrates a front elevational view of portions of a uterus, vagina, uterine arteries, and an exemplary tool, similar to FIG. 4, during a clamping step.

Non-permanent occlusion of the uterine artery is sufficient to cause the demise of uterine myomata without unnecessarily exposing other tissues and anatomical structures to hypoxia attendant to prior permanent occlusion techniques. Burbank, Fred, et al., Uterine Artery Occlusion by Embolization or Surgery for the Treatment of Fibroids: A Unifying Hypothesis-Transient Uterine Ischemia, The Journal of the American Association of Gynecologic Laparoscopists, November 2000, Vol. 7, No. 4 Supplement, pp. S3–S49. While occlusion of a uterine artery can be achieved using procedures which penetrate tissue of the patient, the inventors herein have discovered that occlusion of one or both of the uterine arteries of a patient can be achieved non-invasively, that is, without penetrating tissue of the patient.

In the context of the present invention, a therapeutically effective transient time of occlusion of a uterine artery to treat uterine fibroid tumors is from 1 hour to 1 day (24 hours). Also in the context of the present invention, a therapeutically effective temporary time of occlusion of a uterine artery to treat uterine fibroid tumors is from 1 day (24 hours) to 7 days (168 hours), and preferably is about 3–4 days (72–96 hours).

Methods for non-permanent uterine artery occlusion in accordance with the present invention allow for substantial improvements in safety and efficacy of this procedure over prior techniques. Processes in accordance with the present invention preferably result in death to the entire uterine fibroid cell line, a normal blood supply to the uterus within a short period of time after reestablishment of the blood supply through the uterine artery or arteries, preferably about a week, and no fear of premature menopause and ovarian failure due to particulate embolization of the ovarian artery or ovaries.

Methods for non-permanent uterine artery occlusion of the present invention are all aimed at producing the following events, preferably in the sequence indicated. Blood flow in the uterine artery is slowed or stopped by occluding the artery. This stoppage of blood flow creates a clotting cascade within the artery in a fashion well known to those skilled in the art. Once blood flow has ceased and the vessel is filled with blood clots or thrombus, uterine fibroids, and more particularly the cells of the uterine fibroids, suffer a nearly immediate death because of the cessation of blood flow to them. The uterus becomes anoxic, but is partially supplied by the ovarian arteries and other collateral circulation. This collateral circulation is adequate to keep the uterine tissues alive and allow for it to recover as the total blood flow to the uterus returns to normal.

The thrombus formed within the transiently or temporarily occluded blood vessel is addressed by the blood system with a series of enzymes which attempt to lyse the thrombus. This cycle is predictable and effective, and it can be assisted with various thrombolytic agents such as tissue plasminogen activator (tPA). In order to assure that the thrombus is well formed to occlude the uterine artery in accordance with the processes of the present invention, hemostasis should be maintained for at least about 1 hour to about 24 hours. Therefore, it is preferable that the mechanism which initiates formation of the thrombus, described in greater detail below, stays in place at least 1 hour to 24 hours to provide for the death of the fibroid cell line. After this initial period to initiate and maintain the formation of a thrombus in the artery, preferably about 1–24 hours, the mechanism can be removed. As described in greater detail below, the mechanism for occluding the uterine artery can take any one of a number of forms in accordance with the present invention, and therefore can be removed by a number of ways, including physical removal from the artery. As will be readily appreciated by one of ordinary skill in the art, the present invention is not limited to the specific examples herein of mechanisms which are useful for occluding a uterine artery, and other suitable methods and devices are also within the spirit and scope of the present invention.

Without being limited to a particular theory, the inventors herein believe that the efficacy of the present invention is due, at least in part, to its emulation of what may have been a natural phenomenon, at least among female humans. In the distant past, it is likely that women generally were pregnant much more than is common today, and would have gone through the birthing process and delivery more often and/or more frequently than today. As is well known to those of skill in the art, when the placenta separates from the uterine wall during childbirth, the woman does not (usually) suffer from massive bleeding, even though the huge number of blood vessels connecting the uterus and the placenta have abruptly been severed. Instead, a biological mechanism, which is not well understood, initiates rapid clotting in the blood vessels which had been supplying the placenta with blood, and the bleeding stops.

Upon this massive clotting event, a region of the uterus through which these blood vessels extend is also starved of blood, becoming hypoxic or anoxic. Thus, any fibroids which are also located in this region of the uterus are also starved of blood, and are killed, as described herein. With the historical expectation that women were pregnant and went through childbirth more frequently, and the common understanding that the location of implantation of a fertilized ova in the uterine wall (endometrium) is essentially random, the result is that, over the time period during which a woman can become pregnant, a set of regions of the uterus are cleared of fibroids. Thus, the relatively recent increase in the diagnosis of myomata may be attributable, at least in part, to the (expected) fact that women are pregnant less, and less frequently, and live longer, than historically was the case. Within this framework, the skilled artisan will appreciate that the present invention emulates, in a sense, the biology of childbirth by causing a portion of the uterus, or the entire uterus, to become hypoxic or anoxic.

Steps of methods in accordance with the present invention will now be described with reference to exemplary mechanisms which occlude one or both uterine arteries in order to initiate the clotting cascade which results in thrombus formation. As will be readily apparent to one of ordinary skill in the art, the devices illustrated and described herein are merely exemplary, and numerous devices can be used to perform the methods of the present invention. Thus, while the drawing figures illustrate several types of devices, detailed descriptions of their structures have not been included herein because the exact nature of devices are not critical to performance of the methods according to the present invention.

While it is likely sufficient that the use of only one of the following modalities will result in the occlusion of a uterine artery, it is also within the scope of the present invention to simultaneously or serially employ multiple modalities to occlude a single uterine artery.

The following are merely provided by way of example and not of limitation. Access to the uterine arteries is preferably achieved by invagination of the vaginal wall without significant, and preferably without any, penetration of the patient's tissues, including the vaginal wall.

One or both of the uterine arteries of the patient are occluded using one of the devices and associated procedures described below. The adequacy of the occlusion can then optionally be measured by any process suitable for the measurement of blood flow, e.g., Doppler ultrasound. The time of initial occlusion can then optionally be marked so that the total time of occlusion of the artery can be ascertained. Although it is preferable that both of the patient's uterine arteries are occluded for the minimum time periods necessary to initiate thrombus formation, and more preferable that the occlusion times for both arteries overlap by at least this minimum time, it is also within the scope of the present invention to occlude the uterine arteries serially.

In the context of the present invention, the term "non-invasive" means that tissue or tissues of the patient, on whom the methods of the present invention are performed, are not significantly penetrated, and preferably are not penetrated at all. Thus, "non-invasive" also includes situations in which minor, including incidental, abrasions, lacerations, and the like occur, without purposefully penetrating tissue in order to access the anatomical structure of interest. As such minor penetrations of tissue are commonplace in the medical and surgical arts and are not considered to be invasive, the skilled artisan will readily appreciate the use of the term "non-invasive" in the context of the present invention.

Turning now to the drawing figures, FIGS. 1–11 illustrate portions of a uterus of a patient and some of her adjacent anatomical structures, reference to which can be made for a better understanding of the present invention. The drawing figures diagrammically illustrate a uterus 10 which is afflicted with one or more fibroid tumors 22. The patient's vagina 12 includes the vaginal fornix 14. The cervix 20 extends between the uterine cavity (not illustrated) and the vagina 12. As discussed further herein, the uterine arteries 16a, 16b extend to the uterus 10 and supply the uterus (and the fibroids) with oxygenated blood.

While one of ordinary skill in the art will appreciate that uterine arteries' internal diameters will normally vary within groups of patients, and therefore that the present invention relates to non-permanent occlusion of uterine arteries of various sizes, typically uterine arteries have internal diameters of about 2 mm to about 4 mm prior to (upstream of) the first order branches of the artery at the uterus. The first order branches, typically, have internal diameters of less than 2 mm, with higher order branches having again smaller internal diameters.

The inventors herein have found that the uterine arteries are located, for female humans, adjacent to the vaginal wall, and more specifically are typically within about 2 cm from the vaginal wall at the vaginal fornix 14. This characteristic of the anatomy had not previously been identified in the literature. Furthermore, the inventors herein have discovered that the distance between the vaginal wall (at the fornix) and a uterine artery is shortened upon traction being applied to the cervix 20 in a direction toward the vaginal opening, such as by pulling on the cervix with, e.g., tenaculum or the like. The inventors herein have also discovered that upon invagination of the vaginal wall as described herein, the distance between this part of the uterine arteries 16a, 16b, and the vaginal wall decreases. By way of example and not of limitation, it has been observed by the inventors herein that this distance can be decreased to about 1 cm or less. This decrease in the distance between a uterine artery and the vaginal wall can greatly facilitate the methods of the present invention by increasing the likelihood that the uterine artery of interest can be accessed, even without the aid of location and identification devices such as ultrasound, Doppler ultrasound, MRI, CAT, and the like.

Therefore, while the processes in accordance with the present invention can be performed on a uterine artery prior to the first order branches, the present invention also can be performed on higher order branches with smaller diameter blood vessels. Thus, while the following descriptions reference the uterine artery, the term uterine artery also includes higher order branches of the uterine artery and the non-permanent occlusion of them. As illustrated in the drawing figures, the uterine arteries 16a, 16b extend generally laterally from the outer portions of the uterus in positions close to the vaginal fornix 14.

It has been observed and reported that blood vessel hemostasis of greater than 4 days (96 hours) is necessary to permanently occlude a blood vessel. See Hay, D. L., et al., "Hemostasis in blood vessels after ligation", Am. J. Obstet. Gynecol. 160:3, pp. 737–739 (March 1989), and Brohim, R. M., et al., "Development of independent vessel security after ligation with absorbable sutures or clips", Am. J. Surg., Vol. 165, pp. 345–349 (March 1993), the entire contents of both of which are incorporated by reference in their entireties herein. Thus, as the processes in accordance with the present invention are directed to noninvasive, non-permanent, transient and/or temporary occlusion of the uterine arteries, it is necessary to remove the vessel occlusion at a time prior to the artery closing permanently and after a therapeutically effective time period of hemostasis for the uterine fibroid cell line to have died from the lack of a sufficient blood supply.

Transient Occlusion

After at least 1 hour of occlusion, preferably 1–24 hours, more preferably 4–24 hours, of total occlusion time for a uterine artery, the device, mechanism, or modality by which the artery was occluded is removed, permitting reestablishment of the blood flow through the uterine artery to the uterus. A therapeutically effective transient time of occlusion of a uterine artery to treat uterine fibroid tumors is from 1 hour to 1 day (24 hours). By occluding a uterine artery for a therapeutically effective transient time of occlusion, the blood flow through the uterine artery is slowed sufficiently, and preferably stopped, for a time sufficient for a blood clot to form in the vessels of the uterus and fibroids growing on the uterus. Once the blood clot is formed, the clot itself can assume the task of slowing or stopping blood flow through the uterine artery, and the device, mechanism, or modality which initially slowed or stopped blood flow (described in greater detail below) can be removed. As will be readily appreciated by one of ordinary skill in the art, the clot will then begin to be broken down or lysed by the body. This lysing process can optionally be assisted by a systemic or localized administration of a thrombolytic agent, such as tPA, or the like, if the practitioner elects to do so.

Temporary Occlusion

After at least 1 day (24 hours), preferably 1–7 days, more preferably 3–4 days, of total occlusion time for a uterine artery, the device, mechanism, or modality by which the artery was occluded is removed, permitting reestablishment of the blood flow through the uterine artery to the uterus. Different from transient occlusion discussed above, temporary occlusion does not rely solely on the blood clot formed as a result of the slowing or stoppage of blood flow through the uterine artery. In accordance with the present invention, temporary occlusion benefits from the combination of both the device, mechanism, or modality and the blood clot to limit or stop blood flow through the uterine artery.

In addition to the foregoing steps in the processes of the present invention, removal of a blood clot or thrombus can be accelerated by the use of an agent which lyses the clot, including the administration of tPA to the patient after the therapeutically effective time period.

Turning again to the drawing figures, FIGS. 1–5 illustrate a step according to one exemplary method in accordance with the present invention. As can be seen in FIG. 1, the vaginal wall, because of its inherent elasticity and flexibility, permits a simple clamping tool 100 to invaginate the vaginal wall. The vaginal wall is invaginated toward the uterine artery 16b on two lateral sides of the uterine artery, corresponding to the distalmost ends of the two clamping portions 102a, 102b of the tool 100. The portions 102a, 102b are preferably advanced, and invaginate the vaginal wall, in an open position and spaced apart from each other a distance large enough so that the uterine artery 16b can be positioned between the ends of the clamping portions.

Although not necessary for performance of the methods of the present invention, location of the uterine artery 16b, and verification that the uterine artery is between the ends of the clamping portions 102a, 102b, can be assisted through the use of commonplace imaging and locating tools, such as MRI, fluoroscopy, CAT, ultrasound, Doppler ultrasound, and the like, as will be readily appreciated by one of ordinary skill in the art. As blood flow sensor 103 is shown schematically in FIG. 9. The present invention includes, however, methods wherein the practitioner does not use or rely on such additional tools, and positions the tool 100 relative to the uterine artery 16b based upon the practitioner's knowledge and experience of where the uterine artery is relative to other anatomical features of the patient.

FIGS. 6–9 illustrate a step of an exemplary method in accordance with the present invention after the step illustrated in FIGS. 1–5. In the later step of FIGS. 6–9, the tool 100 has been closed onto the properly positioned uterine artery 16b, and the uterine artery is collapsed by the bilateral force exerted on the uterine artery. More particularly, the portions 102a, 102b exert a combined clamping force on the invaginated vaginal walls 18a, 18b, which exert forces on any tissue between the walls 18a, 18b, which in turn exert forces on the exterior wall of the uterine artery 16b. The force(s) exerted on the wall of the uterine artery are sufficient to collapse the uterine artery, and at least reduce the blood flow rate through the uterine artery to a level sufficient to initiate a clotting sequence. Optionally, the wall of the uterine artery 16b can be completely collapsed, i.e., the blood flow through the uterine artery is zero. As described elsewhere herein, cessation of blood flow through the uterine artery can have therapeutic effects for treating fibroids.

Tool 100 can be any device which can invaginate the vaginal wall as described above, and clamp or press the invaginated vaginal wall to at least partially collapse the uterine artery between the clamping portions of the tool.

Figure 11:
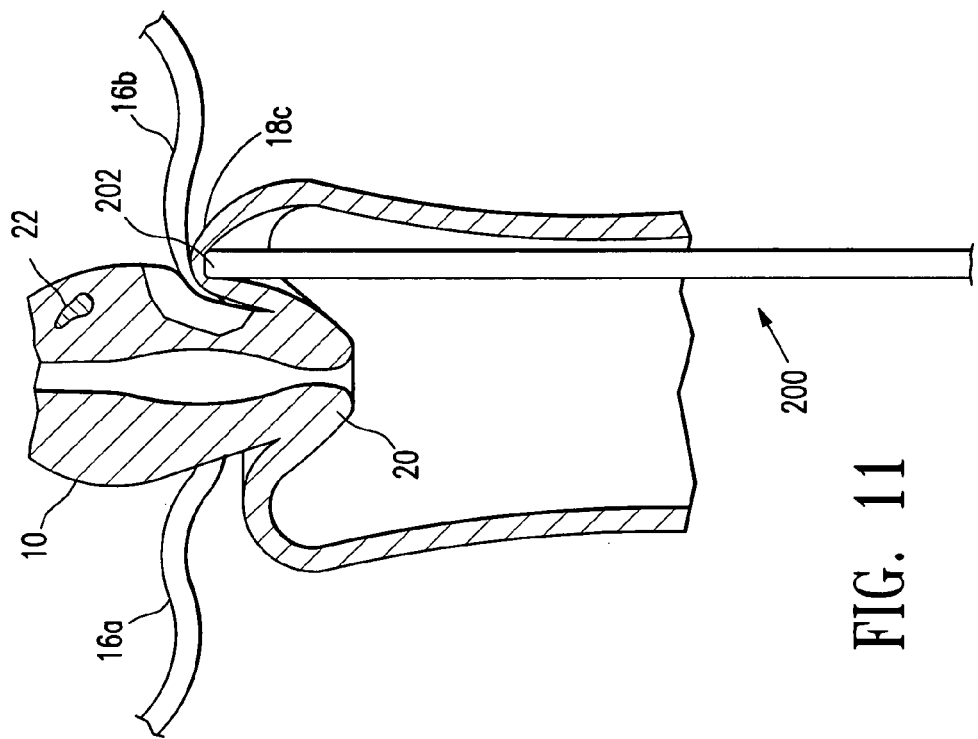
FIG. 11 illustrates a cross-sectional view taken at line 11—11 in FIG. 10.
Figure 10:
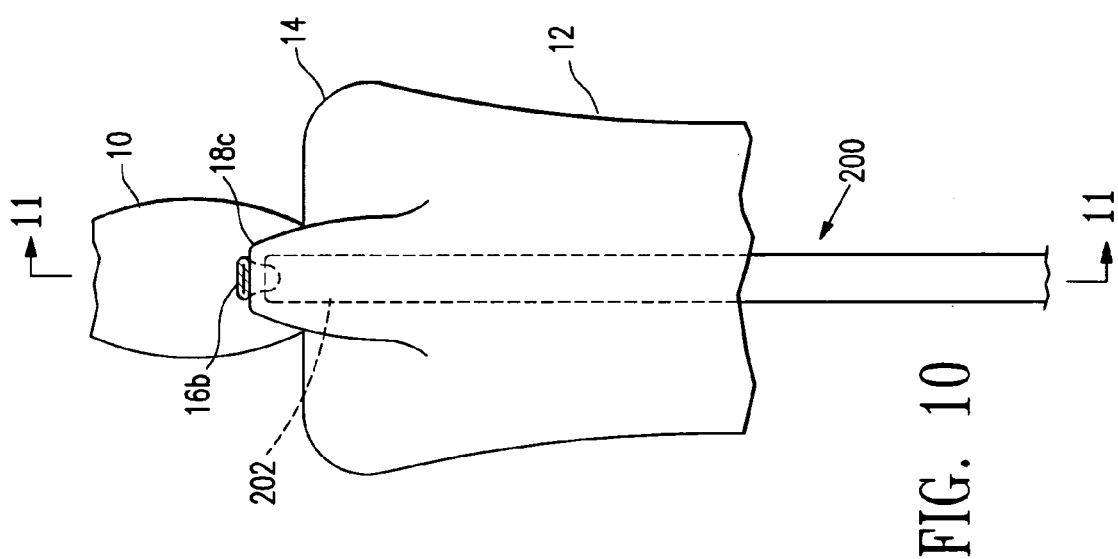
FIG. 10 illustrates a right side elevational view of portions of a uterus, vagina, uterine arteries, and an exemplary tool according to another exemplary embodiment of the invention.

FIGS. 10 and 11 illustrate a step of yet another exemplary method in accordance with the present invention. A tool 200 is used to invaginate the vaginal wall at 18c, and to press against the uterine artery 16b with an end portion 202. As described above, the uterus 10 is oftentimes a fairly muscular, moderately rigid structure. The inventors herein have discovered that the uterus can be used as the second force-exerting member or anvil by which the uterine artery can be collapsed. In the first exemplary embodiment, described above, the two force originating members were portions of a tool 100; in the second exemplary embodiment, the tool 200 is one of the force-originating members, and the uterus itself is the other force-originating member. In this context, the uterus 10 can be likened to an anvil or platen against which a tool presses the uterine artery 16b to collapse it. Thus, tool 200 should have an end 202 which is sufficiently large that, upon invagination of the vaginal wall 18c, the uterine artery 16b can be at least partially collapsed. Of course, tool 200 should not be so large that it is incapable of being inserted into the vaginal fornix 14.

Tool 200 can be any device which can invaginate the vaginal wall as described above, and clamp or press the invaginated vaginal wall 18c to at least partially collapse the uterine artery between the tool and the uterus 10.

The present invention also relates to the treatment of conditions which involve or include uterine bleeding, and more specifically to inhibiting or stopping uterine bleeding altogether. As discussed briefly above, there are numerous known conditions which involve or include uterine bleeding; DUB, PPH, and obstetrical, including cesarian section-related, hemorrhaging, and bleeding during and after a myomectomy, are but a few examples of uterine bleeding which can be inhibited or stopped by methods of the present invention. As described above, the collapse of a uterine artery and the associated hemostasis in the artery will reduce or completely cut off the blood supply to a portion of the uterus; simultaneous collapse of both uterine arteries in a patient reduces or completely cuts off the blood supply to the uterus, and therefore stops uterine bleeding, whatever the cause.

Thus, the present invention extends to any procedure which can benefit from a reduction in the blood flow to and in the uterus of a patient, including a complete cessation of blood flow. As discussed above, it may be appropriate in some procedures, such as hysterectomy, to eventually permanently stop the blood flow through the uterine artery. According to certain aspects of the present invention, hysterectomy can be facilitated by first occluding the uterine artery using methods of the present invention, and thereafter proceeding with other steps of the hysterectomy. As methods of the present invention benefit from the possibility of being rapidly performed, in contrast to the laborious and time-consuming tasks of dissection and ligation of the uterine arteries typically involved with hysterectomy procedures, the entire hysterectomy procedure can be less time consuming. According to this hysterectomy-related embodiment of the present invention, the term therapeutically effective time means the time until the blood flow through the uterine artery is controlled by another modality, such as by permanent ligation of the uterine artery by known techniques. Other procedures to which the methods of the present invention will be readily apparent to those of skill in the art.

As will be readily appreciated by those of skill in the art, it can often be the case that a particular procedure or treatment of a patient, although indicated, in not fully successful in treatment of the patient's condition, and another procedure or treatment is indicated and advisable. In the context of the present invention, there may be instances when non-permanent occlusion of one or both uterine arteries of a patient does not fully alleviate the patient's symptoms and, upon consultation with the medical practitioner, the patient may elect and consent to myomectomy, or partial or complete hysterectomy. Thus, the present invention also extends to methods of performing a myomectomy and/or a hysterectomy, in any form, which are preceded by a step or steps of non-permanent occlusion of a uterine artery, as described herein, well before the myomectomy or hysterectomy.

The foregoing exemplary embodiments of methods in accordance with the present invention are performed on one or all uterine arteries 16a, 16b of the patient. According to the present invention, the same or different specific methods can be performed on different uterine arteries, e.g., bilateral occlusion on uterine artery 16a and unilateral occlusion on uterine artery 16b, or bilateral or unilateral occlusion on both uterine arteries.

While the invention has been described in detail with reference to preferred embodiments thereof, it will be apparent to one skilled in the art that various changes can be made, and equivalents employed, without departing from the scope of the invention. While specific reference has been made to female adult human patients, processes in accordance with the present invention also include occlusion of one or both of the uterine arteries of any female patient that has uterine arteries, including pediatric humans and other mammals, and in particular non-marsupial mammals. Each of the aforementioned published documents are incorporated by reference herein in their entirety.

What is claimed is:

1. A device for treating a uterus of a female patient by occluding at least in pert a uterine artery thereof, comprising:
    a) a first elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw having sufficient area to occlude the patient's uterine artery when pressed against the patient's vaginal fornix and having a tissue receiving recess proximal to the clamping surface;
    b) a second elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw; and
    c) a pivotal connection between the first and second elongated clamping members at a location proximally spaced from the tissue receiving recess; and
    d) a blood flow sensor to detect the patient's uterine artery.

2. The device of claim 1, wherein the first and second elongated clamping members are configured so that the jaws thereof press into a vaginal wall and clamp at least a portion of said vaginal wall between jaws thereof and to at least partially occlude a uterine artery disposed therein.

3. The device of claim 1 including a blood flow sensor configured to verify that the patient's uterine artery is located between the jaws of the first and second elongated damping members.

4. The device of claim 3, wherein the blood flow sensing device is a blood flow sensing device selected from the group consisting of magnetic resonance imaging (MRI) devices, fluoroscopy devices, computer-assisted tomography (CAT) devices, ultrasound devices, and Doppler ultrasound devices.

5. The device of claim 3, wherein the blood flow sensing device comprises a Doppler ultrasound sensing device.

6. The device of claim 1 wherein the second elongated clamping member has a tissue receiving recess proximal to the jaw thereof.

7. A system for treating a uterus of a female patient by at least partially occluding a uterine artery thereof, comprising:
    a) a uterine artery occlusion device having
        a first elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw having sufficient area to at least partially occlude the patients uterine artery when pressed against the patient's vaginal fornix,
        a second elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw,
        a pivotal connection between the first and second elongated clamping members at a location proximally spaced from the tissue receiving recess; and
    b) a blood flow sensing device configured to verify that the patient's uterine artery is located between the jaws of the elongated clamping members.

8. The system of claim 7, wherein the blood flow sensing device is selected from the group consisting of MRI devices, fluoroscopy devices, CAT devices, ultrasound devices, and Doppler ultrasound devices.

9. The system of claim 7, wherein the blood flow sensing device is a Doppler ultrasound sensing device.

10. The system of claim 7, wherein first and second clamping members are configured so that the jaws thereof press into the patient's vaginal wall and clamp at least a portion of said vaginal wall between jaws thereof to at least partially occlude a uterine artery disposed therein.

11. The system of claim 7 wherein the first and second elongated clamping members of the uterine artery occlusion device have tissue receiving recesses proximal to the jaws thereof.

12. A system for treating a uterus of a female patient by at least partially occluding a uterine artery thereof comprising:
    a) a uterine artery occlusion device having
        a first elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw having sufficient area to at least partially occlude a uterine artery when pressed against the patient's vaginal fornix and having a tissue receiving recess proximal to the clamping surface, a second elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw, a pivotal connection between the first and second elongated clamping members at a location proximally spaced from the tissue receiving recess; and b) a sensing device for detecting blood flow through the patient's uterine artery.

13. The system of claim 11. wherein the blood flow sensing device is selected from the group consisting of MRI devices, fluoroscopy devices, CAT devices, ultrasound devices, and Doppler ultrasound devices.

14. A system for treating a uterus of a female patient by at least partially occluding a uterine artery thereat comprising:

a) a uterine artery occlusion device having a first elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw having sufficient area to at least partially occlude a uterine artery when pressed against the patient's vaginal fornix and having a tissue receiving recess proximal to the clamping surface, a second elongated clamping member which has a proximal section forming in part a manually manipulative handle configured to extend out of the patient's vagina when the device is in position to occlude the patient's uterine artery and which has a distal section forming in part a jaw having a pressure applying clamping surface on a distal end of the jaw, a pivotal connection between the first and second elongated clamping members at a location proximally spaced from the tissue receiving recess; and b) a sensing device for locating the patient's uterine artery.

15. The system of claim 14, wherein the blood flow sensing device is selected from the group consisting of MRI devices, fluoroscopy devices, CAT devices, ultrasound devices, and Doppler ultrasound devices.

* * * * *

Dedication 7,223,279 B2 — Fred Burbank, Laguna Niguel, CA (US); Greig E. Altieri, Laguna Beach, CA (US); Michael L. Jones, Capistrano Beach, CA (US). METHODS FOR MINIMALLY-INVASIVE, NON-PERMANENT OCCLUSION OF A UTERINE ARTERY. Patent dated May 29, 2007. Dedication filed November 2, 2011, by the assignee, Vascular Control Systems, Inc.

Hereby dedicates to the Public, the remaining term, including any patent term extension, of said patent.

*(Official Gazette, August 14, 2012)*